United States Patent [19]

Jackson

[11] Patent Number: 4,981,994
[45] Date of Patent: Jan. 1, 1991

[54] PREPARATION OF CYANATE ESTERS

[75] Inventor: Roy J. Jackson, Houston, Tex.

[73] Assignee: Shell Oil Company, Houston, Tex.

[21] Appl. No.: 387,268

[22] Filed: Jul. 31, 1989

[51] Int. Cl.$^5$ ............................................. C07C 261/02
[52] U.S. Cl. ...................................... 560/301; 548/521; 548/549; 549/531
[58] Field of Search ....................... 560/301; 568/654; 548/521, 549; 549/531

[56] References Cited

U.S. PATENT DOCUMENTS

| | | | |
|---|---|---|---|
| 3,107,261 | 10/1963 | Gerber et al. | 260/453 |
| 3,595,900 | 7/1971 | Loudas et al. | 260/453 |
| 3,761,501 | 9/1973 | Woolf et al. | 560/301 |
| 3,876,607 | 4/1975 | Snell et al. | 260/37 EP |
| 3,994,949 | 11/1976 | Meyer et al. | 260/453 P |
| 4,022,755 | 5/1977 | Tanigaichi et al. | 260/59 R |
| 4,026,913 | 5/1977 | Tanigaichi et al. | 260/463 |
| 4,028,393 | 6/1977 | Rottloff et al. | 260/453 P |
| 4,029,649 | 6/1977 | Karrer | 568/654 X |
| 4,046,796 | 9/1977 | Rottloff et al. | 260/453 P |
| 4,060,541 | 11/1977 | Sundermann | 260/453 AR |
| 4,170,711 | 10/1979 | Orlando et al. | 560/301 X |
| 4,226,800 | 10/1980 | Picklesimer | 568/654 X |
| 4,713,442 | 12/1987 | Woo et al. | 528/422 |
| 4,740,584 | 4/1988 | Shimp | 528/422 |
| 4,749,760 | 6/1988 | Wang | 525/471 |
| 4,806,625 | 2/1989 | Bogan et al. | 528/422 |

FOREIGN PATENT DOCUMENTS 877840  11/1959  United Kingdom ............... 560/301

Primary Examiner—Joseph Paul Brust

[57] ABSTRACT

A base-catalyzed process is provided for the preparation of cyanate esters, the process including the step of pre-reacting a phenolic starting material with the basic catalyst and then reacting the pre-reaction product with a cyanogen halide. The process permits the preparation of cyanate esters in high yields at reaction temperatures above room temperature.

14 Claims, No Drawings

PREPARATION OF CYANATE ESTERS

BACKGROUND OF THE INVENTION

This invention relates to the preparation of cyanate esters. In one aspect, the invention relates to a high-temperature method for preparation of cyanate esters.

Cyanate esters are thermosettable materials of interest in electronics applications because of their ease of processability, low dielectric constants and high glass transition temperatures. One drawback of cyanate esters, however, is that their preparation, which involves the base-catalyzed reaction of a cyanogen halide and a phenolic resin, requires such low temperatures, generally in the range of about −10° to 10° C., as to require refrigeration of the reaction mixture. At higher reaction temperatures, the cyanogen halide appears to react with the basic catalyst, competing with the desired reaction of cyanogen halide with the phenolate salt and lowering the yield of cyanate ester product. It would be desirable, for practical as well as economic reasons, to prepare cyanate esters in good yields at a higher temperature.

It is therefore an object of the invention to provide a relatively high-temperature process for the preparation of cyanate esters.

SUMMARY OF THE INVENTION

According to the invention, cyanate esters are prepared by the base-catalyzed reaction of a phenolic compound and a cyanogen halide in a process in which the phenolic reactant is pre-reacted with the catalyst to form a salt, which is then contacted with the cyanogen halide under conditions effective for production of a cyanate ester. The invention process permits the preparation of cyanate esters in good yields at relatively high reaction temperatures.

DETAILED DESCRIPTION OF THE INVENTION

The phenolic reactant can be any aromatic compound containing one or more reactive hydroxyl groups. The phenolic reactant is preferably a di- or polyhydroxy compound of the formula

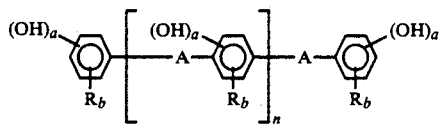

in which each a and b is independently 0, 1, 2 or 3 and at least one a is not 0; n is within the range of 0 to about 8, preferably 0–3; each R is independently selected from non-interfering alkyl, aryl, alkaryl, heteroatomic, heterocyclic, carbonyloxy, carboxy, and the like ring substituents, such as hydrogen, $C_{1-6}$ alkyl, $C_{1-6}$ allyl, halogen, $C_{1-6}$ alkoxy, maleimide, propargyl ether, glycidyl ether, and the like; and A is a polyvalent linking moiety which can be, for example, aromatic, aliphatic, cycloaliphatic, polycyclic, and heteroatomic. Examples of linking moiety A include —O—, —SO$_2$—, —CO—, —OCOO—, —S—, —C$_{1-12}$—, dicyclopentadienyl, aralkyl, aryl, cycloaliphatic and a direct bond.

Such phenolic reactants include, for example, phenol, m-, p-dihydroxy benzene, 2-tert-butyl hydroquinone, 2,4-dimethyl resorcinol, 2,5-di-tert-butyl hydroquinone, tetramethyl hydroquinone, 2,4,6-trimethyl resorcinol, 2,6-di-tert-butyl hydroquinone, 4-chlororesorcinol; dihydroxy naphthalenes such as, for example, 2,4-, 1,5-, 1,6-, 1,7-, 2,6- and 2,7-dihydroxy napthalene; dihydroxy diphenyls such as for example 4,4′-dihydroxy diphenyl, 2,2′-dihydroxy diphenyl, 3,3′,5,5′-tetramethyl-4,4′-dihydroxy diphenyl, 3,3′,5,5′-tetrachloro-4,4′-dihydroxy diphenyl, 3,3′,5,5′-tetrachloro-2,2′-dihydroxy diphenyl, 2,2′,6,6′-tetrachloro-4,4′-dihydroxy diphenyl, 4,4′-bis-[(3-hydroxy)-phenoxy]-diphenyl, 4,4′-bis-[(4-hydroxy)-phenoxy]-diphenyl; 2,2′-dihydroxy-1,1′-binaphthyl; dihydroxy diphenyl ethers such as, for example, 4,4′-dihydroxy diphenyl ether, 3,3′,5,5′-tetramethyl-4,4′-dihydroxy diphenyl ether, 3,3′,5,5′-tetrachloro-4,4′-dihydroxy diphenyl ether, 4,4′-bis-[p-hydroxy phenoxy]-diphenyl ether, 4,4′-bis-[p-hydroxyphenyl isopropyl]-diphenyl ether, 4,4′-bis-[p-hydroxyphenoxy]-benzene, 4,4′-bis-[m-hydroxy phenoxy]-diphenyl ether, 4,4′-bis-[4-(4-hydroxy phenoxy)-phenylsulphone]-diphenyl ether; diphenyl sulphones such as, for example, 4,4′-dihydroxy diphenyl sulphone 3,3′,5,5′-tetramethyl-4,4′-dihydroxy diphenyl sulphone, 3,3′,5,5′-tetrachloro-4,4′-dihydroxy diphenyl sulphone, 4,4′-bis-[p-hydroxy phenyl isopropyl]-diphenyl sulphone, 4,4′-bis-[(4-hydroxy)-phenoxy]-diphenyl sulphone, 4,4′-bis-[(3-hydroxy)-phenoxy]-diphenyl sulphone, 4,4′-bis-[4(4-hydroxy phenyl isopropyl)-phenoxy]-diphenyl sulphone, 4,4′-bis-[4-(4-hydroxy phenyl sulphone)-phenoxy]-diphenyl sulphone, 4,4′-bis-[4-(4-hydroxy)-diphenoxy]-diphenyl sulphone; dihydroxy diphenyl alkanes such as, for example, 4,4′-dihydroxy diphenyl methane, 4,4′-bis-[p-hydroxy phenyl]-diphenyl methane, 2,2-bis(p-hydroxyphenyl)propane, 2,2-bis-(3,5-dimethyl-4-hydroxy phenyl)-propane, 2,2-bis-(3,5-dichloro-4-hydroxy phenyl)-propane, 1,1-bis-[p-hydroxy phenyl]-cyclohexane, bis-[2-hydroxy-1-naphthyl]-methane, 1,2-bis-[p-hydroxy phenyl]-1,1,2,2-tetramethyl ethane, 4,4′-dihydroxy benzophenone, 4,4′-bis-(4-hydroxy)-phenoxy benzophenone, 1,4-bis-[p-hydroxy phenyl isopropyl]-benzene, phloroglucinol and 2,2′,5,5′-tetrahydroxy diphenyl sulphone.

Phenolic reactants can also include phenolic novolacs, such as BPA novolac and o-cresol novolac, for example. The phenolic novolac may contain substituents as described above, including glycidyl ether, propargyl ether and $C_{1-6}$ alkyl groups.

The reaction of the cyanogen halide with a phenol is catalyzed by a base. The base can be, for example, an alkali metal hydroxide such as sodium hydroxide or potassium hydroxide; an alkali metal alkylate such as sodium methylate or potassium methylate; and various amines, preferably tertiary amines.

The basic catalyst is preferably a tertiary amine. Tertiary amines can be represented by the formula

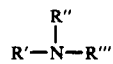

in which R′, R″ and R‴ represent $C_{1-36}$, preferably $C_{1-10}$ alkyl; aryl such as phenyl; and $C_{4-7}$ cycloalkyl. Examples of such tertiary amines include trimethyl amine, triethyl amine, methyl diethyl amine, tripropyl amine, tributyl amine, methyl dibutyl amine, dinonyl methyl amine, dimethyl stearyl amine, dimethyl cyclohexyl amine and diethyl aniline. The preferred tertiary amine, because of its availability and catalytic activity, is triethylamine.

In general, although the quantity can vary widely depending on reaction conditions, the basic catalyst is generally employed in a quantity of at least about 0.7 equivalent, preferably about 0.9 to about 1.5 equivalents, per equivalent of the hydroxyl groups to be converted to a cyanic acid ester group (—OC≡N).

The phenolic reactant and the base are pre-reacted prior to contact of the phenolic reactant and the cyanogen halide. The pre-reaction will generally be carried out in an organic solvent, including ketones such as methyl ethyl ketone, acetone and methyl isobutyl ketone; aliphatic alcohols such as methanol, ethanol, propanol and butanol; amides such as dimethyl formamide and dimethyl acetamide; cyclic ethers such as dioxane and tetrahydrofuran; aromatic hydrocarbons such as benzene, toluene or xylene and mixtures of such organic solvents. Water may also be used as a medium for the pre-reaction.

The pre-reaction temperature can vary depending upon the other reaction conditions, but will generally be carried out at a temperature greater than about 30° C., preferably within the range of about 40° to about 80° C. Pressure can vary but will most conveniently be atmospheric. The time for completion of the reaction will vary depending upon the other reaction conditions, but will generally be within the range of about 1 to about 3 hours. Mild stirring is generally used.

The preparation of the cyanate ester will be carried out by reacting the salt pre-reaction product with a cyanogen halide. The preferred cyanogen halides, because of their availability, are cyanogen chloride and cyanogen bromide. The reaction is preferably carried out in a solvent, such as those described above for the pre-reaction, under an inert atmosphere such as nitrogen gas. The reaction temperature can vary within the range of about −20° C. to the boiling temperature of the reactants, but will most conveniently and with highest yields be carried out at a temperature above about 20° C., preferably within the range of about 20° to about 60° C., most preferably about 20° to 45° C.

The product cyanate ester can be recovered from the reaction mixture by methods such as filtration or centrifugation followed by washing.

In a specific embodiment of the invention process, mixed-functionality aromatic compounds having at least one cyanate ester group and at least one propargyl ether group (—OCH$_2$C≡CH) are prepared by the base-catalyzed reaction of a phenolic compound having at least one propargyl ether substituent with a cyanogen halide, in a process which involves pre-reaction of the basic catalyst and the substituted phenol. Such a substituted phenol can be prepared, for example, by reacting a phenolic starting material with less than an equivalent amount of a propargyl halide in an aqueous alkaline solution.

In a preferred method, a phenolic such as bisphenol-A or a phenolic novolac, for example, is contacted with propargyl chloride or propargyl bromide in an aqueous sodium hydroxide reaction medium also containing a co-solvent which provides good phase separation. Suitable solvents include aromatic hydrocarbons such as toluene, alcohols such as isopropyl alcohol, and ketones such as methyl isobutyl ketone. The reaction is generally carried out at a temperature in the range of about 40° to about 80° C. The resulting propargyl ether having free hydroxyl groups is then pre-reacted with the basic catalyst, preferably a tertiary amine, at a temperature within the range of about 30° to about 80° C. The resulting salt is then reacted with cyanogen chloride or cyanogen bromide in an organic solvent such as methyl isobutyl ketone at a temperature within the range of about −20° C. to about 60° C., preferably about 20° to about 45° C., and atmospheric pressure. The by-product amine hydrohalide salts can be removed by filtration or like means. The product aromatic propargyl ether having cyanate ester substituents can be recovered by conventional techniques such as distillation, precipitation or solvent extraction, depending upon the specific product.

EXAMPLE 1

Preparation of Cyanate Ester

To a 250 ml four-neck round-bottom flask equipped with a stirrer, condenser, nitrogen inlet tube, addition funnel and thermocouple were added 14 grams of bisphenol-A dissolved in 70 ml of methyl isobutyl ketone. The temperature was raised to 40° C. and 12.9 grams of triethylamine were added dropwise. After the addition had been completed, the mixture was heated for one hour at 70° C. After heating had been completed, the mixture was transferred to a dropping funnel on another four-neck flask equipped as the first. In the second flask, 19.9 grams of cyanogen bromide was added and dissolved with stirring in 50 ml of methyl isobutyl ketone. The temperature was raised to 40° C. and the previously-reacted triethylamine and BPA mixture was added dropwise over the next two hours. The course of the reaction was followed by IR. The IR spectrum initially showed the cyanate band of cyanogen bromide at 2220 cm$^{-1}$, followed by the gradual appearance of a band at 2300 cm$^{-1}$ representing the cyanate ester of BPA. There was little evidence of the presence of diethylcyanamide, which has an IR band at 2260 cm$^{-1}$. This example confirms that, by pre-reacting the triethylamine and the BPA, a cyanate ester product can be prepared at relatively high reaction temperature.

EXAMPLE 2

Comparison Preparation of Cyanate Ester

A comparison experiment was performed to prepare a cyanate ester without pre-reaction of the triethylamine catalyst with the BPA. The reaction described in Example 1 was essentially duplicated without the pre-reaction step. The triethylamine and BPA were dissolved in methyl isobutyl ketone at room temperature and added dropwise to cyanogen bromide dissolved in methyl isobutyl ketone at 40° C. The initial IR showed the cyanate band of cyanogen bromide at 2200 cm followed by the gradual appearance of the diethylcyanamide band at 2260 cm$^{-1}$. Unlike the run using pre-reacted triethylamine and BPA, there was little evidence of BPA cyanate formation.

EXAMPLE 3

Preparation of Cyanate Ester

This example illustrates the preparation of a cyanate ester according to the invention process using somewhat higher pre-reaction and reaction temperatures than those of inventive Example 1.

Into a 4-neck, 500 ml round-bottom flask equipped with a stirring rod, dropping funnel, nitrogen inlet tube, thermocouple and condenser were added 50 g (0.22 moles) of BPA and 250 ml methyl isobutyl ketone. The temperature was increased to 60° C., and 45 g (0.445 moles) of triethylamine were added dropwise over one hour. Heating was continued for an additional 1.25 hours.

The pre-reacted mixture was then transferred to a dropping funnel attached to a 2000 ml reaction flask equipped as described above. Into the flask were added 69.6 g (0.66 moles) of cyanogen bromide and 200 ml of methyl isobutyl ketone. The mixture was stirred until the cyanogen bromide was dissolved and the temperature was raised to 47° C. The pre-reacted solution was added to the cyanogen bromide dropwise over an hour. The reaction began to turn cloudy after about 30 minutes, and one could visually observe the presence of triethylamine hydrobromide after one hour. The reaction was stirred without heat overnight. The precipitated triethylamine hydrobromide was removed by filtration and the solvent was vacuum distilled off. Yield of BPA dicyanate was about 90%, based upon recovered triethylamine hydrobromide.

EXAMPLE 4

Preparation of Propargyl Cyanate Ester

Functionalized cyanate esters can be prepared by the invention process at relatively high temperatures, as illustrated by the following experiment. Propargyl ethers containing cyanate ester functional groups were prepared in a process employing a pre-reaction step at 45° C. and reaction temperatures of 40° C. and 60° C.

Into a 5000 ml, 4-neck flask equipped with a stirrer, reflux condenser and thermocouple were added 2055 g of methyl isobutyl ketone and 240 g water. 353.7 g of o-cresylic novolac resin having a molecular weight of 625 and average hydroxyl functionality of 5 were added to the flask, which was then heated to 40° C. After the o-cresylic novolac resin was completely dissolved, 119 g of 50% solution of sodium hydroxide in water was slowly added over 40 minutes at 40° C. After hydroxide addition was complete, the temperature was raised to 60° C. and 279 g of propargyl chloride were added slowly over 2.7 hours. After propargyl chloride addition was complete, the temperature was increased to reflux (78° C.) and maintained for 3 hours. The reaction mixture was stirred overnight. The aqueous phase was removed.

217.5 g of the organic phase was weighed into a 500 ml 4-neck flask and to this was added 12.6 g triethylamine at 45° C. The resulting solution was divided into two equal portions. Each portion was added dropwise to a solution of 9.9 g cyanogen bromide in 30 g methyl isobutyl ketone. The temperature of the first solution was maintained at 45° C. for 1 hour. The temperature of the second solution was maintained at 60° C. for 1 hour. Both reaction mixtures were stirred at room temperature overnight. The products were recovered by vacuum distillation. Uncatalyzed gel time of the products (unwashed) were 257 seconds and 66 seconds, respectively. Each product showed an IR band at 2300 cm$^{-1}$.

I claim:

1. A process for preparing a cyanate ester comprising the steps of:
    (a) contacting, at a temperature within the range of about 40° to about 80° C., (i) a phenolic compound which can be represented by the formula

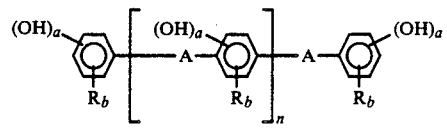

in which each a and b is independently 0, 1, 2 or 3 and at least one a is not 0; n is within the range of 0 to about 8; each R is selected independently from hydrogen, $C_{1-6}$ alkyl, $C_{1-6}$ allyl, halide, $C_{1-6}$ alkoxy, maleimide, propargyl ether, glycidyl ether, and phenyl; and A is a divalent linking moiety, and (ii) a tertiary amine which can be represented by the formula

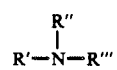

in which R', R" and R''' are independently selected from $C_{1-10}$ alkyl, phenyl and $C_{1-7}$ cycloalkyl, under conditions effective for production of a reaction product of said phenolic compound and said tertiary amine; and subsequently
    (b) contacting, at a temperature within the range of about 20° to 60° C., said reaction product and a cyanogen halide under conditions effective for preparation of a cyanate ester.

2. The process of claim 1 in which the tertiary amine is selected from the group consisting of trimethyl amine, triethyl amine, methyl diethyl amine, tripropyl amine, tributyl amine, methyl dibutyl amine, dinonyl methyl amine, dimethyl stearyl amine, dimethyl cyclohexyl amine and diethyl aniline.

3. The process of claim 1 in which the cyanogen halide is selected from the group consisting of cyanogen chloride and cyanogen bromide.

4. The process of claim 3 in which the tertiary amine is triethyl amine.

5. The process of claim 1 in which the phenolic compound is selected from the group consisting of phenol, dihydroxy benzene and 2,2-bis(p-hydroxyphenyl)propane.

6. The process of claim 1 in which the phenol can be described by the formula

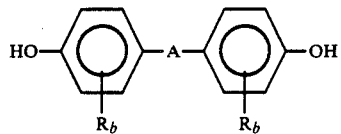

in which A is $C_{1-3}$ alkyl, each R is selected from hydrogen, halide and $C_{1-3}$ alkylene and b is 0, 1, 2 or 3.

7. The process of claim 1 in which the phenolic compound is a phenolic novolac.

8. The process of claim 1 in which the base is triethylamine.

9. The process of claim 8 in which step (b) is carried out in methyl isobutyl ketone solvent.

10. The process of claim 1 which further comprises the step of recovering a solid cyanate ester.

11. A process for preparing an aromatic cyanate ester having propargyl ether substituents, the process comprising:

(a) contacting (i) a phenolic compound which can be represented by the formula

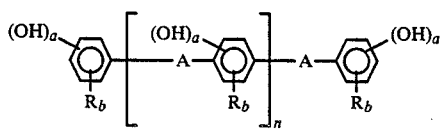

in which each a and b is independently 0, 1, 2 or 3 and at least one a is not 0; n is within the range of 0 to about 8; each R is selected independently from hydrogen, $C_{1-6}$ alkyl, $C_{1-6}$ allyl, halide, $C_{1-6}$ alkoxy, maleimide, propargyl ether, glycidyl ether, and phenyl and at least one R is propargyl ether; and A is a divalent linking moiety, and (ii) less than an equivalent amount, based on phenolic hydroxyl groups, of a propargyl halide in a basic reaction medium under conditions effective to produce a phenolic product having propargyl ether substituents;

(b) reacting, at a temperature within the range of about 40° to about 80° C., said phenolic product with at least about 0.7 equivalent, based on remaining phenolic hydroxyl groups, of a tertiary amine which can be represented by the formula

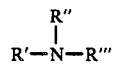

in which R', R" and R'" are selected independently from $C_{1-10}$ alkyl, phenyl and $C_{1-7}$ cycloalkyl, under conditions effective for production of a reaction product of said phenolic compound and said tertiary amine; and subsequently (c) contacting said reaction production and a cyanogen halide in a liquid reaction medium at a temperature within the range of about 20° to about 60° C. to produce said aromatic cyanate ester having propargyl ether substitutents.

12. The process of claim 11 in which the tertiary amine is triethylamine.

13. The process of claim 11 in which the phenolic compound is selected from 2,2-bis(p-hydroxyphenyl)-propane and phenolic novolacs.

14. The process of claim 11 in which the tertiary amine of step (b) comprises triethylamine.

* * * * *